United States Patent
Emoto et al.

(10) Patent No.: US 9,421,534 B2
(45) Date of Patent: Aug. 23, 2016

(54) PRODUCTION METHOD OF α-OLEFIN LOW POLYMER

(75) Inventors: Hiroki Emoto, Kurashiki (JP); Kei Yoshizuru, Kurashiki (JP)

(73) Assignee: MITSUBISHI CHEMICAL CORPORATION, Tokyo (JP)

(*) Notice: Subject to any disclaimer, the term of this patent is extended or adjusted under 35 U.S.C. 154(b) by 119 days.

(21) Appl. No.: 12/520,096

(22) PCT Filed: Oct. 22, 2007

(86) PCT No.: PCT/JP2007/070572
§ 371 (c)(1),
(2), (4) Date: Jun. 19, 2009

(87) PCT Pub. No.: WO2008/081638
PCT Pub. Date: Jul. 10, 2008

(65) Prior Publication Data
US 2009/0326297 A1 Dec. 31, 2009

(30) Foreign Application Priority Data
Dec. 28, 2006 (JP) .................................. 2006-354541

(51) Int. Cl.
*C07C 2/08* (2006.01)
*C07C 2/02* (2006.01)
(Continued)

(52) U.S. Cl.
CPC ............ *B01J 31/2208* (2013.01); *B01J 31/143* (2013.01); *C07C 2/08* (2013.01); *C08F 10/00* (2013.01); *B01J 2231/12* (2013.01);
(Continued)

(58) Field of Classification Search
USPC ......... 585/502, 510, 511, 512, 513, 520, 521, 585/522, 527
See application file for complete search history.

(56) References Cited

U.S. PATENT DOCUMENTS 2,860,126 A 11/1958 Cines
2,964,511 A * 12/1960 Cottle ............................. 526/61
(Continued)

FOREIGN PATENT DOCUMENTS

EP 0 887 359 A1 12/1998
GB 855120 11/1960
(Continued)

OTHER PUBLICATIONS

Edgar, et al., "Process Control" in Perry's Chemical Engineer's Handbook, 7th ed., R. H. Green and D. W. Perry, eds., McGraw-Hill, 1997, available on-line at www.knovel.com on Mar. 1, 2001.*
(Continued)

*Primary Examiner* — In Suk Bullock
*Assistant Examiner* — Youngsul Jeong
(74) *Attorney, Agent, or Firm* — Oblon, McClelland, Maier & Neustadt, L.L.P.

(57) ABSTRACT

A method of producing an α-olefin low polymer, wherein an α-olefin is subjected to low polymerization in a solvent in the presence of a chromium catalyst and at least one inert gas. The proportion of the inert gas is maintained from 0.010 to 50.00% by volume in a gas phase part of a reactor, such that inert gas is discharged from the reactor and/or circulation piping when the proportion exceeds 50.00%. The chromium catalyst contains a chromium compound, at least one nitrogen-containing compound, an aluminum-containing compound, and optionally a halogen-containing compound. Unreacted α-olefin and solvent separated from a reaction liquid are circulated back into the reactor.

12 Claims, 2 Drawing Sheets

(51) Int. Cl.
*C07C 2/04* (2006.01)
*C07C 2/42* (2006.01)
*C07C 2/54* (2006.01)
*C07C 2/72* (2006.01)
*B01J 31/22* (2006.01)
*B01J 31/14* (2006.01)
*C08F 10/00* (2006.01)

(52) U.S. Cl.
CPC ........... *B01J2231/20* (2013.01); *B01J 2531/62* (2013.01); *Y02P 20/52* (2015.11)

(56) References Cited

U.S. PATENT DOCUMENTS

| | | | | |
|---|---|---|---|---|
| 3,250,757 | A * | 5/1966 | Smith et al. | 526/60 |
| 4,434,313 | A * | 2/1984 | Langer, Jr. | 585/527 |
| 5,198,563 | A * | 3/1993 | Reagen et al. | 556/57 |
| 5,518,527 | A | 5/1996 | Tomizuka et al. | |
| 5,689,028 | A * | 11/1997 | Lashier et al. | 585/512 |
| 5,705,577 | A * | 1/1998 | Rossi et al. | 526/68 |
| 5,750,816 | A * | 5/1998 | Araki et al. | 585/512 |
| 5,856,612 | A | 1/1999 | Araki et al. | |
| 6,380,451 | B1 * | 4/2002 | Kreischer et al. | 585/502 |
| 6,593,506 | B1 * | 7/2003 | Searle | 585/639 |
| 7,157,612 | B2 * | 1/2007 | Ewert et al. | 585/511 |
| 2003/0027947 | A1 | 2/2003 | Kobayashi et al. | |
| 2003/0153798 | A1 | 8/2003 | Kobayashi et al. | |
| 2005/0256357 | A1 | 11/2005 | Mihan et al. | |
| 2006/0063896 | A1 | 3/2006 | McElvain et al. | |
| 2006/0180024 | A1 * | 8/2006 | Nishida et al. | 95/141 |
| 2007/0088186 | A1 * | 4/2007 | Forestiere et al. | 585/504 |

FOREIGN PATENT DOCUMENTS

| | | |
|---|---|---|
| JP | 7 10788 | 1/1995 |
| JP | 7 60048 | 3/1995 |
| JP | 7 324047 | 12/1995 |
| JP | 8 239419 | 9/1996 |
| JP | 10 45833 | 2/1998 |
| JP | 10 101724 | 4/1998 |
| JP | 11 60511 | 3/1999 |
| JP | 11 71411 | 3/1999 |
| JP | 2002 255863 | 9/2002 |
| JP | 2002 256007 | 9/2002 |
| JP | 2003 64105 | 3/2003 |
| JP | 2008-179631 | 8/2008 |
| WO | WO 02/04119 A1 | 1/2002 |
| WO | WO 2006/026493 A1 | 3/2006 |
| WO | WO 2006/108934 A2 | 10/2006 |

OTHER PUBLICATIONS

D. R. Lide, ed., CRC Handbook of Chemistry and Physics, 91st ed., 2011 Internet Version.*
Seador, et al., "Distillation" in Perry's Chemical Engineer's Handbook, 7th ed., McGraw-Hill (1997), R. H. Perry and D. W. Green, eds., available on-line at www.knovel.com.*
Belanger, P. W., "Plantwide Design and Control of Processes with Light, Intermediate, and Heavy Inerts", Ph.D dissertation, Lehigh University, 1997, abstract only—month unknown.*
Naqvi, "1-Hexene from Ethylene by the Phillips Trimerization Technology", SRI Consulting PEP Review Jan. 8, 1995, Dec. 1997.*
U.S. Appl. No. 12/519,778, filed Jun. 18, 2009, Yokoyama, et al.
U.S. Appl. No. 12/519,525, filed Jun. 17, 2009, Emoto, et al.
U.S. Appl. No. 12/521,467, filed Jun. 26, 2009, Emoto, et al.
Office Action issued Mar. 4, 2011, in Eurasian Patent Application No. 200970640 with English translation.
Egyptian Office Action issued Aug. 21, 2010 in corresponding Egyptian Application No. PCT 1008/2009 filed Jun. 28, 2009 (with English Translation).
Extended European Search Report issued Feb. 7, 2011 in the corresponding European Patent Application No. 07830306.2.
Office Action issued Dec. 17, 2010, in Singapore Patent Application No. 200903970-2.
Office Action issued Dec. 31, 2010, in China Patent Application No. 200780045028.5 (with English translation).
Dictionary of Chemical Engineering, Chemical Industry Press, 1$^{st}$ Ed., Aug. 31, 1970, pp. 524-525.
Office Action issued Jan. 27, 2012, in Eurasian Patent Application No. 200970640 with English translation.
Office Action issued Dec. 7, 2011, in European Patent Application No. 07 830 306.2.
Office Action issued Jun. 18, 2013, in European Patent Application No. 07 830 306.2.
Office Action issued Sep. 6, 2013 in Canadian Application No. 2,672,385.
Notification of Reasons for Refusal issued in corresponding Japanese Patent Application No. 2008-326605 dated May 26, 2009 (w/English translation).
Final Rejection issued in corresponding Japanese Patent Application No. 2008-326605 dated Aug. 25, 2009 (w/English translation).
Notification of Reasons for Refusal issued in corresponding Japanese Patent Application No. 2008-326605 dated Apr. 10, 2012 (w/English translation).
Office Action issued in corresponding Indian Patent Application No. 1098/MUMNP/2009 dated Aug. 28, 2012.
Office Action issued Aug. 29, 2012 in European Patent Application No. 07 830 306.2-2109.
Office Action dated Feb. 12, 2013 issued in corresponding Japanese patent application No. 2007-341365 (w/English translation).
Office Action issued Dec. 24, 2013 in Indian Patent Application No. 1089/MUMNP/2009.
Office Action issued Aug. 6, 2013 in Japanese Patent Application No. 2007-341365 with English language translation.
Office Action issued May 22, 2015 in Eurasian Patent Application No. 200970640 (with English translation).

* cited by examiner

PRODUCTION METHOD OF α-OLEFIN LOW POLYMER

CROSS-REFERENCE TO RELATED APPLICATIONS

This application is a National Stage of PCT/JP2007/070572 filed on Oct. 22, 2007. This application is based upon and claims the benefit of priority to Japanese Application No. 2006-354541 filed on Dec. 28, 2006, the entire contents of which are hereby incorporated by reference.

BACKGROUND OF THE INVENTION

1. Technical Field

The present invention relates to a production method of an α-olefin low polymer. More particularly, it relates to a production method of an α-olefin low polymer, which obtains the α-olefin low polymer in high yield.

2. Background Art

Conventionally, a production method in which an α-olefin low polymer such as 1-hexene is selectively obtained using an α-olefin such as ethylene as a raw material and using a chromium series catalyst is known.

For example, Patent Document 1 reports a production method in which an α-olefin low polymer mainly comprising 1-hexene is obtained in high yield and high selectivity using a chromium series catalyst comprising a chromium compound (a), a nitrogen-containing compound (b) such as an amine and an alkyl aluminum compound (c).

Furthermore, Patent Document 2 reports a method of preventing adhesion of a by-produced polymer to a reactor and an external cooling apparatus by setting a liquid circulation amount and temperature of a cooling medium in the external cooling apparatus to specific ranges in producing an α-olefin low polymer mainly comprising 1-hexene using a chromium series catalyst having the similar composition and using a reaction apparatus which has a circulation passing through the external cooling apparatus from the reactor.

Patent Document 1: JP-A-08-239419
Patent Document 2: JP-A-11-060511

DISCLOSURE OF THE INVENTION

Problems that the Invention is to Solve

To produce an α-olefin low polymer inexpensively by subjecting an α-olefin such as ethylene to low polymerization reaction in a solvent using a chromium series catalyst, an unreacted α-olefin and a solvent are separated from a reaction liquid obtained by the low polymerization reaction of an α-olefin, and the unreacted α-olefin and solvent separated from the reaction liquid are circulated to a reactor.

However, when the operation of circulating the unreacted α-olefin and solvent separated from the reaction liquid to a reactor is repeated, there is the problem that conversion of from an α-olefin to an α-olefin low polymer is decreased.

Where an α-olefin such as ethylene is subjected to low polymerization reaction using a chromium series catalyst, a catalyst solution and a solvent are generally supplied to a reactor from a drum in an inert gas atmosphere such as nitrogen or a rare gas in order to prevent deactivation of catalyst components. In this case, a slight amount of an inert gas dissolved in the catalyst solution and the solvent is introduced into a reactor. Where the operation of circulating an unreacted α-olefin and the solvent separated from the reaction liquid into the reactor is repeated, an inert gas concentration in the reaction system is excessively increased. As a result, there are the problems that a relative concentration of an α-olefin such as ethylene used as a raw material is decreased, and additionally, the conversion of from an α-olefin into an α-olefin low polymer is decreased.

In particular, it is expected the demand for 1-hexene largely increases as mainly a comonomer of a linear low density polyethylene. For this reason, a production method of obtaining an α-olefin low polymer in high yield is required.

The present invention has been made to solve the above-described problems in the production method of an α-olefin low polymer.

Accordingly, an object of the present invention is to provide a production method of an α-olefin low polymer in which a low polymer of an α-olefin is obtained in high yield.

Means for Solving the Problems

As a result of extensive and intensive investigations to solve the above problems, the present inventors have reached the present invention. That is, the gist of the present invention resides in the following items (1) to (8).

(1) A production method of an α-olefin low polymer which comprises subjecting an α-olefin to low polymerization in a solvent supplied to a reactor in the presence of a chromium series catalyst, characterized in that:

an inert gas is allowed to exist in a gas phase of the reactor in the proportion of from 0.010 to 50.00% by volume, an unreacted α-olefin and the solvent are separated from a reaction liquid obtained by the low polymerization reaction of an α-olefin, and the unreacted α-olefin and the solvent separated from the reaction liquid are circulated into the reactor.

(2) The production method of an α-olefin low polymer described in (1), characterized in that the inert gas is nitrogen, a rare gas or a mixture thereof.

(3) The production method of an α-olefin low polymer described in (1) or (2), characterized in that the inert gas is discharged outside the reaction system from a gas phase part of the reactor and/or the circulation piping of the unreacted α-olefin (including a gas phase part of equipment).

(4) The production method of an α-olefin low polymer described in any one of (1) to (3), characterized in that the solvent separated from the reaction liquid obtained by the low polymerization reaction of an α-olefin is circulated into the reactor without passing through a solvent drum.

(5) The production method of an α-olefin low polymer described in any one of (1) to (4), characterized in that the chromium series catalyst is constituted of a combination of at least a chromium compound (a), a nitrogen-containing compound (b) and an aluminum-containing compound (c).

(6) The production method of an α-olefin low polymer described in any one of (1) to (4), characterized in that the chromium series catalyst is constituted of a combination of at least a chromium compound (a), a nitrogen-containing compound (b), an aluminum-containing compound (c) and a halogen-containing compound (d).

(7) The production method of an α-olefin low polymer described in (1), characterized in that the low polymerization of an α-olefin is conducted in a state that the chromium compound (a) and the aluminum-containing compound (c) are not previously contacted.

(8) The production method of an α-olefin low polymer described in (1), characterized in that the α-olefin is ethylene.

According to the present invention, a production method of an α-olefin low polymer which comprises low polymerizing an α-olefin in a solvent supplied to a reactor in the presence of a chromium series catalyst, characterized in that an inert gas is allowed to exist in a gas phase of a reactor in the proportion of from 0.010 to 50.00% by volume, an unreacted α-olefin and the solvent are separated from a reaction liquid obtained by low polymerization reaction of an α-olefin, and the unreacted α-olefin and the solvent separated from the reaction liquid are circulated into the reactor, is provided.

In the production method of an α-olefin low polymer to which the present invention is applied, the inert gas used is preferably nitrogen, a rare gas or a mixture of those.

Furthermore, in the production method of an α-olefin low polymer to which the present invention is applied, where the proportion of the inert gas present in the gas phase exceeds 50.00% by volume, the inert gas is preferably discharged outside the reaction system from a gas phase part of the reactor and/or the circulation piping of the unreacted α-olefin (including a gas phase part of an equipment).

Moreover, when the solvent separated from the reaction liquid obtained by the low polymerization reaction of an α-olefin is again returned to the reactor, and the solvent is circulated and used, the solvent to be circulated is preferably directly returned to the reactor through the circulation piping without passing through a solvent drum.

In the production method of an α-olefin low polymer to which the present invention is applied, the chromium series catalyst is preferably constituted of a combination of at least a chromium compound (a), a nitrogen-containing compound (b) and an aluminum-containing compound (c).

Furthermore, the chromium series catalyst is more preferably constituted of a combination of at least a chromium compound (a), a nitrogen-containing compound (b), an aluminum-containing compound (c) and a halogen-containing compound (d).

In the production method of an α-olefin low polymer to which the present invention is applied, the low polymerization of an α-olefin is preferably conducted in a state that the chromium compound (a) and the aluminum-containing compound (c) are not previously contacted. When the low polymerization of an α-olefin is conducted in such a state, trimerization reaction of an α-olefin is selectively conducted, and an α-olefin low polymer such as 1-hexene is obtained in high yield.

In the present invention, the α-olefin is preferably ethylene.

Advantage of the Invention

According to the present invention, an α-olefin low polymer can be produced in high yield.

DESCRIPTION OF REFERENCE NUMERALS AND SIGNS

Figure 1:
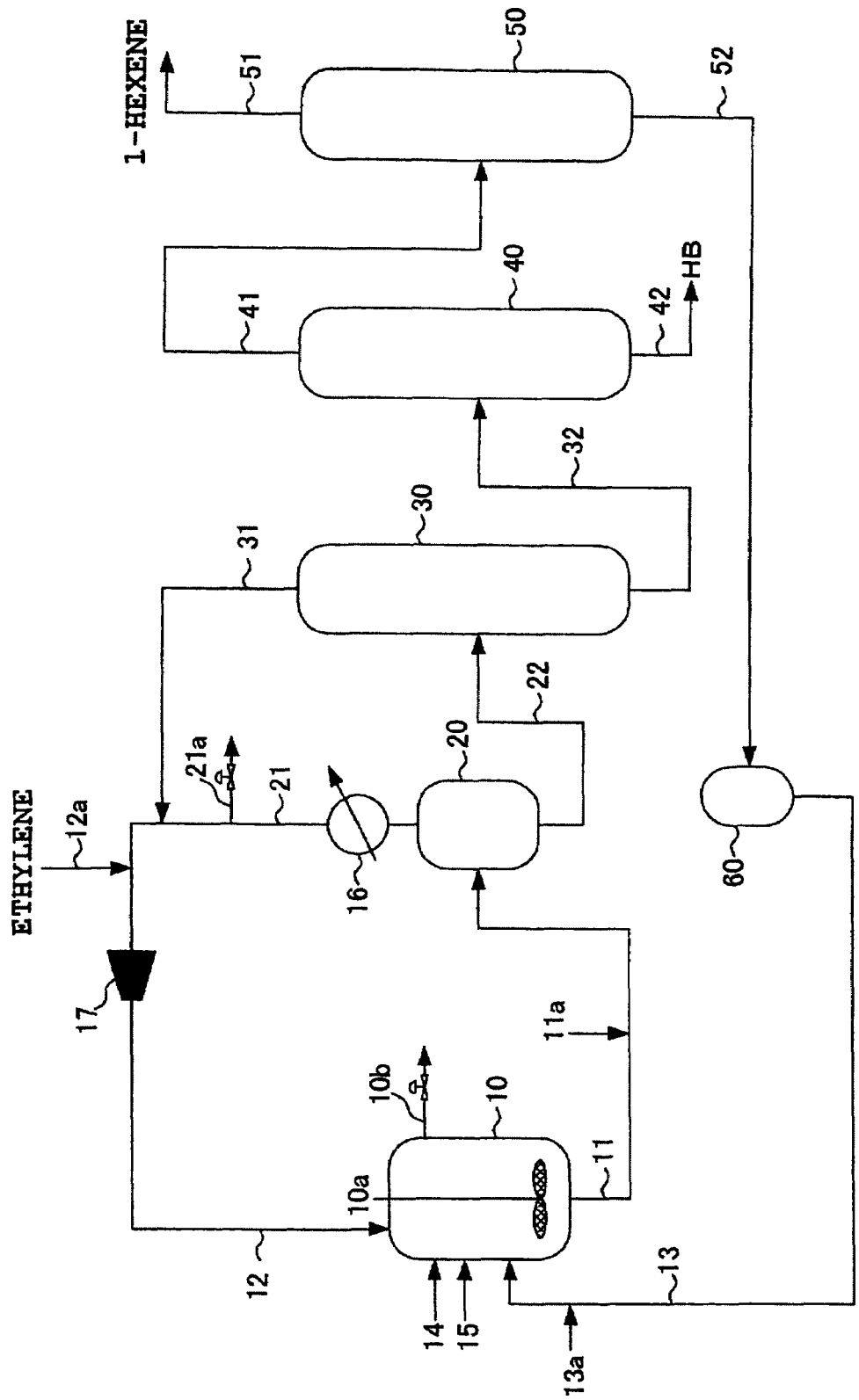
FIG. 1 is a view explaining a production flow example of an α-olefin low polymer in the embodiment of the invention.

10 . . . Reactor
10a . . . Stirring machine
10b . . . Gas discharge line
11, 22, 32, 41, 42, 51 . . . Piping
11a . . . Deactivator supply piping
12 . . . First supply piping
12a . . . Ethylene supply piping
13 . . . Second supply piping
13a . . . Catalyst supply piping
14 . . . Third supply piping
15 . . . Fourth supply piping
21, 31 . . . Circulation piping
21a . . . Gas discharge line
16 . . . Condenser
17 . . . Compressor
20 . . . Degassing tank
30 . . . Ethylene separation column
40 . . . High boiling separation column
50 . . . Hexene separation column
52 . . . Solvent circulation piping
60 . . . Solvent drum

BEST MODE FOR CARRYING OUT THE INVENTION

The best mode for carrying out the invention (hereinafter, the embodiment of the invention) is described in detail below. The invention is not limited to the following embodiment, and can be carried out with various modifications within a scope of its gist. Furthermore, the drawings used are to explain the present embodiment, and do not show the actual size.

(α-Olefin)

In the production method of an α-olefin low polymer to which the embodiment of the invention is applied, the α-olefin used as a raw material includes substituted or unsubstituted α-olefins having from 2 to 30 carbon atoms. Specific examples of such an α-olefin include ethylene, propylene, 1-butene, 1-hexene, 1-octene, 3-methyl-1-butene and 4-methyl-1-pentene. In particular, ethylene is preferred as the α-olefin of a raw material, and when ethylene is used as the raw material, 1-hexene as a trimer of ethylene is obtained in high yield and high selectivity. Furthermore, when ethylene is used as the raw material, impurity components other than ethylene may be contained in the raw material. Specific impurity components include methane, ethane, acetylene and carbon dioxide. Those components are preferably in an amount of 0.1 mol % or less based on ethylene of the raw material. The α-olefin low polymer used herein means a polymer comprising 2 to 10 of α-olefin as a monomer being bonded.

(Chromium Series Catalyst)

The chromium series catalyst is descried below. The chromium series catalyst used in the embodiment of the invention includes a catalyst constituted of a combination of at least a chromium compound (a), at least one nitrogen-containing compound (b) selected from the group consisting of an amine, an amide and an imide, and an aluminum-containing compound (c).

The chromium series catalyst used in the embodiment of the invention may contain a halogen-containing compound (d) as a fourth component according to need. Each component is described below.

(Chromium Compound (a))

The chromium compound (a) used in the embodiment of the invention includes at least one compound represented by the general formula $CrX_n$. In the general formula, X represents an optional organic group or inorganic group, or a negative atom, and n is an integer of from 1 to 6, and is preferably 2 or more. When n is 2 or more, X may be the same or different.

Examples of the organic group include a hydrocarbon group having from 1 to 30 carbon atoms, a carbonyl group, an alkoxy group, a carboxyl group, a β-diketonate group, a β-ketocarboxyl group, a β-ketoester group and an amide group.

Examples of the inorganic group include chromium salt-forming groups such as a nitric acid group or a sulfuric acid group. Examples of the negative atom include oxygen and a halogen. A halogen-containing chromium compound is not included in the halogen-containing compound (d) described hereinafter.

The number of valency of chromium (Cr) is 0 to 6. The preferred chromium compound (a) includes a carboxylate of chromium (Cr). Specific examples of the carboxylate of chromium include chromium (II) acetate, chromium (III) acetate, chromium (III)-n-octanoate, chromium (III)-2-ethylhexanoate, chromium (III) benzoate and chromium (III) naphthenate. Of those, chromium (III)-2-ethylhexanoate is particularly preferred.

(Nitrogen-Containing Compound (b))

The nitrogen-containing compound (b) used in the embodiment of the invention includes at least one compound selected from the group consisting of an amine, an amide and an imide. Examples of the amine include a primary amine compound, a secondary amine compound and a mixture of those. Examples of the amide include a metal amide compound derived from a primary amine compound or a secondary amide compound, a mixture of those, and an acid amide compound. Examples of the imide include 1,2-cyclohexanedicarboxylmide, succinimide, phthalimide, maleimide and those metal salts.

The preferred nitrogen-containing compound (b) used in the embodiment of the invention includes a secondary amine compound. Examples of the secondary amine compound include pyrroles such as pyrrole, 2,4-dimethylpyrrole, 2,5-dimethylpyrrole, 2-methyl-5-ethylpyrrole, 2,5-di-methyl-3-ethylpyrrole, 3,4-dimethylpyrrole, 3,4-dichloro-pyrrole, 2,3,4,5-tetrachloropyrrole and 2-acetylpyrrole, and their derivatives. Examples of the derivative include metal pyrrolide derivatives. Specific examples of the metal pyrrolide derivative include diethylaluminum pyrrolide, ethylaluminum dipyrrolide, aluminum tripyrrolide, sodium pyrrolide, lithium pyrrolide, potassium pyrrolide, diethylaluminum(2,5-dimethyl-pyrrolide), ethylaluminum bis(2,5-dimethylpyrrolide), aluminum tris(2,5-dimethylpyrrolide), sodium(2,5-dimethyl-pyrrolide), lithium(2,5-dimethylpyrrolide) and potassium-(2,5-dimethylpyrrolide). Of those, 2,5-dimethylpyrrole and diethylaluminum(2,5-dimethylpyrrolide) are preferred. (Here, the aluminum pyrrolides are not included in the aluminum-containing compound (c). Furthermore, the halogen-containing pyrrole compound (b) is not included in the halogen-containing compound (d).)

(Aluminum-Containing Compound (c))

The aluminum-containing compound (c) used in the embodiment of the invention includes at least one compound such as a trialkylaluminum compound, an alkoxyalkyl-aluminum compound and a hydrogenated alkylaluminum compound. Specific examples thereof include trimethyl-aluminum, triethylaluminum, triisobutylaluminum, diethylaluminum ethoxide and diethylaluminum hydride. Of those, triethylaluminum is particularly preferred.

(Halogen-Containing Compound (d))

The chromium series catalyst used in the embodiment of the invention contains the halogen-containing compound (d) as the fourth component according to need. Examples of the halogen-containing compound (d) include at least one compound of a halogenated alkylaluminum compound, a linear halohydrocarbon having 3 or more halogen atoms and a cyclic halohydrocarbon having 3 or more carbon atoms and having 3 or more halogen atoms. (The halogenated alkylaluminum compound is not included in the aluminum-containing compound (c)). Specific examples thereof include diethylaluminum chloride, ethylaluminum sesquichloride, carbon tetrachloride, 1,1,1-trichloro-ethane, 1,1,2,2-tetrachloroethane, pentachloroethane, hexachloroethane, 1,2,3-trichlorocyclopropane, 1,2,3,4,5,6-hexachlorocyclohexane and 1,4-bis(trichloro-methyl)-2,3,5,6-tetrachlorobenzene.

In the embodiment of the invention, the low polymerization of an α-olefin is preferably that the chromium compound (a) and the aluminum-containing compound (c) are not previously contacted, or an α-olefin and the chromium series catalyst are previously contacted in a state that the previous contact time is short. Such a contact embodiment makes it possible to selectively conduct trimerization reaction of ethylene, thereby obtaining 1-hexene from ethylene as a raw material in high yield.

The contact embodiment in the above continuous reaction system includes the following (1) to (9).

(1) A method of simultaneously introducing a mixture of the catalyst components (a), (b) and (d) and the catalyst component (c) into a reactor, respectively.

(2) A method of simultaneously introducing a mixture of the catalyst components (b) to (d) and the catalyst component (a) into a reactor, respectively.

(3) A method of simultaneously introducing a mixture of the catalyst components (a) and (b) and a mixture of the catalyst components (c) and (d) into a reactor, respectively.

(4) A method of simultaneously introducing a mixture of the catalyst components (a) and (d) and a mixture of the catalyst components (b) and (c) into a reactor, respectively.

(5) A method of simultaneously introducing a mixture of the catalyst components (a) and (b), catalyst component (c) and the catalyst component (d) into a reactor, respectively.

(6) A method of simultaneously introducing a mixture of the catalyst components (c) and (d), catalyst component (a) and the catalyst component (b) into a reactor, respectively.

(7) A method of simultaneously introducing a mixture of the catalyst components (a) and (d), catalyst component (b) and the catalyst component (c) into a reactor, respectively.

(8) A method of simultaneously introducing a mixture of the catalyst components (b) and (c), catalyst component (a) and the catalyst component (d) into a reactor, respectively.

(9) A method of simultaneously and independently introducing each of the catalyst components (a) to (d).

The above-described each catalyst component is generally dissolved in a solvent used in the reaction, and supplied to a reactor.

The "embodiment that the chromium compound (a) and the aluminum-containing compound (c) are not previously contacted" is not limited to the initiation time of the reaction, and means that such an embodiment is maintained even in the supply of the subsequent additional α-olefin and catalyst components into the reactor.

Furthermore, in a batch reaction type, it is desired that the same embodiment is utilized.

The ratio of each constituent in the chromium series catalyst used in the embodiment of the invention is generally that the nitrogen-containing compound (b) is from 1 to 50 moles, and preferably from 1 to 30 moles, per mole of the chromium compound (a), and the aluminum-containing compound (c) is from 1 to 200 moles, and preferably from 10 to 150 moles, per mole of the chromium compound. When the halogen-containing compound (d) is contained in the chromium series catalyst, the halogen-containing compound (d) is from 1 to 50 moles, and preferably from 1 to 30 moles, per mole of the chromium compound (a).

In the embodiment of the invention, the amount of the chromium series catalyst used is not particularly limited, but is generally from $1.0 \times 10^{-7}$ to 0.5 mole, preferably from $5.0 \times 10^{-7}$ to 0.2 mole, and further preferably from $1.0 \times 10^{-6}$ to 0.05 mole, in terms of chromium atom of the chromium compound (a) per 1 liter of the solvent described hereinafter.

By using such a chromium series catalyst, for example when ethylene is used as a raw material, hexene which is a trimer of ethylene can be obtained in selectivity of 90% or more. In this case, the proportion of 1-hexene occupied in hexene can be 99% or more.

(Solvent)

In the production method of an α-olefin low polymer to which the embodiment of the invention is applied, the reaction of an α-olefin can be conducted in a solvent.

Such a solvent is not particularly limited. However, for example, chain saturated hydrocarbons or alicyclic saturated hydrocarbons, having from 1 to 20 carbon atoms, such as butane, pentane, 3-methylpentane, hexane, heptane, 2-methylhexane, octane, cyclohexane, methylcyclohexane, 2,2,4-trimethylpentane and decalin; and aromatic hydrocarbons such as benzene, toluene, xylene, ethylbenzene, mesitylene and tetralin are used. Furthermore, an α-olefin low polymer may be used as a solvent. Those can be used alone or as a mixed solvent.

In particular, the preferred solvent is chain saturated hydrocarbons or alicyclic saturated hydrocarbons, having from 4 to 10 carbon atoms. When those solvents are used, by-produced polymers such as a polyethylene can be suppressed. Furthermore, when the alicyclic saturated hydrocarbons are used, high catalyst activity tends to be obtained.

(Production Method of α-Olefin Low Polymer)

The production method of an α-olefin low polymer is described by referring to an example of the production of 1-hexene which is a trimer of ethylene as an α-olefin low polymer using ethylene as an α-olefin.

FIG. 1 is a view explaining a production flow example of an α-olefin low polymer in the embodiment of the invention. The production flow example of 1-hexene using ethylene as a raw material shown in FIG. 1 shows a completely mixing and stirring type reactor 10 in which ethylene is subjected to low polymerization in the presence of a chromium series catalyst, a degassing tank 20 that separates an unreacted ethylene gas from a reaction liquid withdrawn from the reactor 10, an ethylene separation column 30 that distills ethylene in the reaction liquid withdrawn from the degassing tank 20, a high boiling separation column 40 that separates substances with a higher boiling point (hereinafter referred to as "HB" (high boiler)) in the reaction liquid withdrawn from the ethylene separation column 30, and a hexene separation column 50 that distills the reaction liquid withdrawn from the top of the high boiling separation column 40 to distill away 1-hexene.

Furthermore, a compressor 17 that circulates an unreacted ethylene separated in the degassing tank 20 and the condenser 16 into the reactor 10 via a circulation piping 21 is provided.

In FIG. 1, the reactor 10 includes the conventional reactor equipped with a stirring machine 10a, baffle, jacket and the like. As the stirring machine 10a, a stirring blade of the type such as paddle, pfaudler, propeller, turbine or the like is used in combination with a baffle such as a planar plate, a cylinder or a hairpin coil.

As shown in FIG. 1, ethylene is continuously supplied to the reactor 10 from an ethylene supply piping 12a via a compressor 17 and the first supply piping 12. Where the compressor 17 is, for example, two-stage compression system, a circulation piping 31 is connected to the first stage, and a circulation piping 21 is connected to the second stage, thereby making it possible to reduce electricity consumption. On the other hand, the chromium compound (a) and the nitrogen-containing compound (b) are supplied from the second supply piping 13 via a catalyst supply piping 13a, the aluminum-containing compound (c) is supplied from the third supply piping 14, and the halogen-containing compound (d) is supplied from the fourth supply piping 15. Furthermore, a solvent used in low polymerization reaction of ethylene is supplied to the reactor 10 from the second supply piping 13.

In the embodiment of the invention, the reaction temperature in the reactor 10 is generally from 0 to 250° C., preferably from 50 to 200° C., and more preferably from 80 to 170° C.

The reaction pressure is in a range of generally from normal pressures to 250 kgf/cm$^2$, preferably from 5 to 150 kgf/cm$^2$, and more preferably from 10 to 100 kgf/cm$^2$.

The trimerization reaction of ethylene is preferably conducted such that a molar ratio of 1-hexene to ethylene in the reaction liquid ((1-hexene in reaction liquid)/(ethylene in reaction liquid)) is from 0.05 to 1.5, and particularly from 0.10 to 1.0. Specifically, it is preferred that in the case of a continuous reaction, a catalyst concentration, reaction pressure and other conditions are adjusted such that the molar ratio of 1-hexene to ethylene in the reaction liquid is in the above range, and in the case of a batchwise reaction, the reaction is stopped at the time that the molar ratio is in the above range. This has the tendency that by-production of compounds having a boiling point higher than that of 1-hexene is suppressed, thereby further increasing selectivity of 1-hexene.

The reaction liquid continuously withdrawn from the bottom of the reactor 10 via a piping 11 is that trimerization reaction of ethylene is stopped by a deactivator supplied from a deactivator supply piping 11a, and such a reaction liquid is supplied to the degassing tank 20. In the degassing tank 20, unreacted ethylene is degassed from the top thereof, and circulated and supplied to the reactor 10 via the circulation piping 21, the condenser 16, the compressor 17 and the first supply piping 12. The reaction liquid from which unreacted ethylene has been degassed is withdrawn from the bottom of the degassing tank 20.

Operation conditions of the degassing tank 20 are that the temperature is generally from 0 to 250° C., and preferably from 50 to 200° C., and the pressure is generally from normal pressures to 150 kgf/cm$^2$, and preferably from normal pressures to 90 kgf/cm$^2$.

Subsequently, the reaction liquid from which unreacted ethylene gas has been degassed in the degassing tank 20 is withdrawn from the bottom of the degassing tank 20, and supplied to an ethylene separation column 30 by a piping 22. In the ethylene separation column 30, ethylene is distilled away from the column top by distillation, and circulated and supplied to the reactor 10 via the circulation piping 31 and the first supply piping 12. The reaction liquid from which ethylene has been removed is withdrawn from the bottom.

Operation conditions of the ethylene separation column 30 are that the top pressure is generally from normal pressures to 30 kgf/cm$^2$, and preferably from normal pressures to 20 kgf/cm$^2$, and the reflux ratio (R/D) is generally from 0 to 500, and preferably from 0.1 to 100.

The reaction liquid from which ethylene has been distilled away in the ethylene separation column 30 is withdrawn from the bottom of the ethylene separation column 30, and supplied to a high boiling separation column 40 by a piping 32. In the high boiling separation column 40, components with high boiling point (HB: high boiler) are withdrawn from the bottom by a piping 42. A distillate from which high boiling components have been separated is withdrawn from the top by a piping 41.

Operation conditions of the high boiling separation column 40 are that the top pressure is generally from 0.1 to 10 kgf/ cm$^2$, and preferably from 0.5 to 5 kgf/cm$^2$, and the reflux ratio (R/D) is generally from 0 to 100, and preferably from 0.1 to 20.

Subsequently, the reaction liquid withdrawn as a distillate from the top of the high boiling separation column 40 is supplied to a hexene separation column 50 by the piping 41. In the hexene separation column 50, 1-hexene is distilled away by distillation from the top by a piping 51. Heptane is withdrawn from the bottom of a hexene separation column 50, and stored in a solvent drum 60 via a solvent circulation piping 52, and circulated and supplied as a reaction solvent to the reactor 10 via the second supply piping 13.

Operation conditions of the hexene separation column 50 are that the top pressure is generally from 0.1 to 10 kgf/cm$^2$, and preferably from 0.5 to 5 kgf/cm$^2$, and the reflux ratio (R/D) is generally from 0 to 100, and preferably from 0.1 to 20.

(Inert Gas Concentration in Gas Phase Part in Reactor)

In the embodiment of the invention, in subjecting ethylene to low polymerization in the presence of a chromium series catalyst in a reactor 10 to produce 1-hexene, an inert gas is allowed to exist in the gas phase part of the reactor 10 in the proportion of from 0.010 to 50.00% by volume. The proportion of the inert gas being allowed to exist in the gas phase part of the reactor is preferably from 0.020 to 40.00% by volume, more preferably from 0.050 to 30.00% by volume, further preferably from 0.500 to 10.00% by volume, and most preferably from 1.000 to 5.000% by volume.

A method of measuring an inert gas concentration in the gas phase part of the reactor 10 is not particularly limited. In general, the concentration can be obtained from a value measured by a gas chromatography mass spectrometer (GC-MS). The gas phase part of the reactor 10 generally contains ethylene gas as a raw material, a catalyst decomposition product, a partially volatiled reaction solvent, an α-olefin low polymer and the like. Ethane, methane, acetylene, carbon dioxide and the like that are contained as impurity components in the raw material ethylene may be contained.

The inert gas is not particularly limited so long as it does not react with a chromium series catalyst and does not change into other compound by the action of the chromium series catalyst. The inert gas generally includes nitrogen, argon and helium, and of those, nitrogen is preferred.

Where the proportion of the inert gas existing in the gas phase part of the reactor 10 is excessively large, the reactivity of an α-olefin such as ethylene tends to decrease. Where the proportion of the inert gas existing in the gas phase part of the reactor 10 is excessively small, the amount of an α-olefin discharged outside the system tends to increase.

A method of allowing to exist the inert gas in the gas phase of the reactor 10 is not particularly limited. For example, the following methods are exemplified. A method in which each component of the chromium series catalyst (the chromium compound (a), the nitrogen-containing compound (b) such as an amine, the aluminum-containing compound (c) and the halogen-containing compound (d)) is previously sealed with an inert gas, and when each component of those is supplied to the reactor 10 via the catalyst supply piping 13*a*, the second supply piping 13, the third catalyst supply piping 14 and the fourth supply piping 15, respectively, the inert gas is supplied to the reactor 10 together with each component; and a method in which when a solvent sealed with an inert gas is supplied to the reactor 10 via the second supply piping 13, the inert gas is supplied to the reactor 10 together with the solvent.

In the embodiment of the invention, the inert gas is required to exist in the gas phase part of the reactor 10 in the proportion of from 0.010 to 50.00% by volume as described before.

Where the proportion of the inert gas in the gas phase exceeds 50.00% by volume, the proportion of the inert gas in the gas phase part is adjusted to 50.00% by volume or less by a given operation.

The operation for adjusting the proportion of the inert gas in the gas phase is not particularly limited. In general, the proportion can be adjusted by discharging the inert gas outside the reaction system operating a valve while monitoring the concentration of the inert gas in the reactor 10.

The place from which the inert gas is withdrawn may be any place if it is the place at which the inert gas exists in the reaction system. The inert gas is preferably withdrawn outside the system together with an α-olefin from the place at which the inert gas is liable to accumulate in the reaction system or an unreacted ethylene circulation line.

For example, the following methods are exemplified. A method in which a valve in a gas discharge line 10*b* set to the reactor 10 is opened, and the inert gas together with an α-olefin are directly discharged outside the reaction system from the gas phase part of the reactor 10; and a method in which a valve in a gas discharge line 21*a* set to the circulation piping 21 for circulating unreacted ethylene separated from the degassing tank 20 into the reactor 10 is opened, and the inert gas together with an α-olefin are discharged outside the reaction system.

Where the raw material ethylene contains ethane, methane, acetylene, carbon dioxide and the like as impurity components, those components are discharged outside the reaction system when the inert gas is discharged together with the α-olefin. According to need, the amount of the inert gas discharged outside the reaction system may be adjusted while monitoring the concentration of those components in addition to the inert gas concentration in the gas phase part of the reactor 10.

The above-described operations can be carried out independently, respectively, and can be carried out by combining those.

Figure 2:
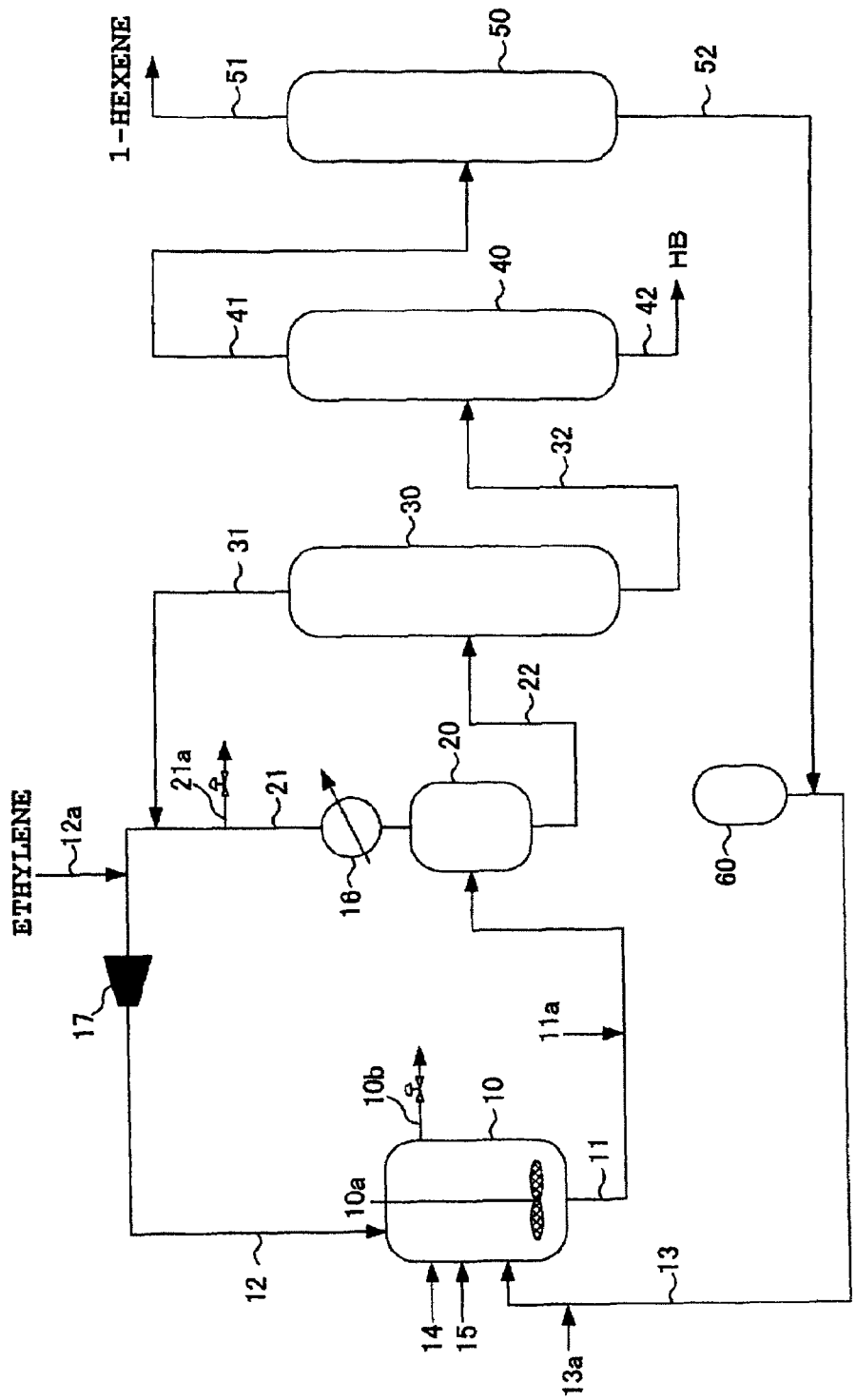
FIG. 2 is a view explaining other production flow example of an α-olefin low polymer.

FIG. 2 is a view explaining other production flow example of an α-olefin low polymer. The same numerical references and signs are used with respect to the structure common to the production flow example of FIG. 1.

In the production flow example shown in FIG. 2, other end of the solvent circulation piping 52 connected to the bottom of the hexene separation column 50 is not connected to the solvent drum 60, but connected to the second supply piping 13 at the discharge side of the solvent drum 60.

By this, heptane obtained from the bottom of the hexene separation column 50 can directly be circulated into the reactor 10 without passing through the solvent drum 60. The inert gas existing in the gas phase part of the solvent drum 60 can be prevented from being dissolved in the reaction solvent circulated into the reactor 10. As a result, the residual inert gas is not supplied to the reactor 10, and the concentration of the inert gas contained in the gas phase part of the reactor 10 can be prevented from being increased more than necessary.

EXAMPLES

The present invention is described further specifically based on the examples. However, the present invention is not limited to the following examples so far as it does not depart from its gist.

Example 1

A continuous low polymerization reaction of ethylene is carried out in a process having the completely mixing and stirring type reactor 10, the degassing tank 20, the ethylene separation column 30, the high boiling separation column 40, the hexene separation column 50 and the solvent drum 60 which stores a circulation solvent, wherein the other end of the solvent circulation piping 52 connected to the bottom of the hexene separation column 50 is connected to the second supply piping 13, thereby by-passing the solvent drum 60, as shown in FIG. 2.

From the first supply piping 12, unreacted ethylene separated from the degassing tank 20 and the ethylene separation column 30 are continuously supplied together with ethylene freshly supplied from the ethylene supply piping 12a to the reactor 10 by the compressor 17. From the second piping 13, the recovered n-heptane solvent separated in the hexene separation column 50 by-passes the solvent drum 60 (2 kgf/cm² nitrogen seal), and is continuously supplied to the reactor 10 at a flow rate of 34 liters/hr.

Next, the n-heptane solution containing chromium (III) 2-ethylhexanoate (a) and 2,5-dimethylpyrrole (b) is supplied from the catalyst supply piping 13a at a flow rate of 0.1 liter/hr, and is continuously supplied to the reactor 10 via the second supply piping 13. The n-heptane solution of triethylaluminum (c) is continuously supplied to the reactor 10 from the third supply piping 14 at a flow rate of 0.03 liter/hr. Furthermore, the n-heptane solution of hexachloroethane (d) is continuously supplied to the reactor 10 from the fourth supply piping 15 at a flow rate of 0.02 liter/hr.

The solution of each of catalyst components is supplied from a nitrogen seal tank (not shown) of 2 kgf/cm².

The catalyst is continuously supplied to the reactor 10 such that the molar ratio of each component is (a):(b):(c):(d)=1:6:40:4. The reaction conditions are 140° C. and 71 kgf/cm².

2-Ethylhexanol as a metal solubilizing agent is added to the reaction liquid continuously withdrawn from the reactor 10 from the deactivator supply piping 11a at a flow rate of 0.005 liter/hr, and such a reaction liquid is then successively treated in the degassing tank 20, the ethylene separation column 30, the high boiling separation column 40 and the hexene separation column 50.

In this process, the nitrogen concentration in the gas phase part of the reactor 10 is obtained by the measurement with a gas chromatography mass spectrometer (GC-MS). A valve in the gas discharge line 10b set to the reactor 10 is opened such that this value is 0.070% by volume, a gas is continuously discharged from the gas phase part of the reactor 10, and ethylene loss ratio (ETY loss ratio) and catalyst efficiency (CE) are obtained. The results are shown in Table 1.

The ethylene loss ratio (ETY loss ratio) is the proportion (PETY/SETY) of ethylene weight PETY (unit: g/hr) discharged outside the system to ethylene weight SETY (unit: g/hr) freshly supplied. Disappearance amount of ethylene is small as the value is small.

The catalyst efficiency (CE) is a product weight (unit: g) produced in 1 hour per chromium atom weight (unit: g) of the catalyst component supplied in 1 hour. The catalyst efficiency is high as the value is large.

Examples 2 to 6, and Comparatives 1 and 2

According to the process of Example 1, a continuous low polymerization reaction of ethylene is carried out, the amount of gas discharged from the gas discharge line 10b set to the reactor 10 is changed such that a nitrogen concentration in the gas phase part of the reactor 10 is the value shown in Table 1, and the ethylene loss ratio (ETY loss ratio) and the catalyst efficiency (CE) are obtained. The results are shown in Table 1.

TABLE 1

| | | Nitrogen concentration in gas phase part of reactor (% by volume) | ETY loss ratio (%) | Catalyst efficiency (CE) |
|---|---|---|---|---|
| Example | 1 | 0.070 | 2.4 | 520000 |
| | 2 | 0.240 | 0.83 | 520000 |
| | 3 | 1.200 | 0.17 | 510000 |
| | 4 | 5.000 | 0.038 | 480000 |
| | 5 | 13.40 | 0.015 | 430000 |
| | 6 | 26.50 | 0.008 | 350000 |
| Comparative Example | 1 | 69.20 | 0.003 | 110000 |
| | 2 | 0.005 | 28 | 520000 |

It is seen from the results shown in Table 1 that when the concentration of nitrogen contained in the gas phase of the reactor 10 is in a range of from 0.010 to 50.00% by volume (0.070 to 26.50% by volume: Examples 1 to 6), the ETY loss ratio is low, and the catalyst efficiency is high.

Contrary to this, when the concentration of nitrogen contained in the gas phase of the reactor 10 is 69.20% by volume which is not less than 50.00% by volume (Comparative Example 1), the catalyst efficiency is decreased. Furthermore, when the concentration of nitrogen contained in the gas phase of the reactor 10 is 0.005% by volume which is not more than 0.010% by volume (Comparative Example 2), the ETY loss ratio is increased.

Examples 7 to 9, and Comparatives 3 and 4

According to the process of Example 1, a continuous low polymerization reaction of ethylene is carried out, the amount of gas discharged from the gas discharge line 21a set to the circulation piping 21 is changed such that nitrogen concentration in the gas phase part of the reactor 10 is the value shown in Table 2, and the ethylene loss ratio (ETY loss ratio) and the catalyst efficiency (CE) are obtained. The results are shown in Table 2.

TABLE 2

| | | Nitrogen concentration in gas phase part of reactor (% by volume) | ETY loss ratio (%) | Catalyst efficiency (CE) |
|---|---|---|---|---|
| Example | 7 | 12.00 | 0.021 | 440000 |
| | 8 | 28.50 | 0.010 | 330000 |
| | 9 | 1.200 | 0.210 | 510000 |
| Comparative Example | 3 | 68.50 | 0.005 | 110000 |
| | 4 | 0.005 | 30 | 520000 |

It is seen from the results shown in Table 2 that when the concentration of nitrogen contained in the gas phase of the reactor 10 is in a range of from 0.010 to 50.00% by volume (1.200 to 28.50% by volume: Examples 7 to 9), the ETY loss ratio is low, and the catalyst efficiency is high.

Contrary to this, when the concentration of nitrogen contained in the gas phase of the reactor 10 is 68.50% by volume which is not less than 50.00% by volume (Comparative Example 3), the catalyst efficiency is decreased. Furthermore, when the concentration of nitrogen contained in the gas phase of the reactor 10 is 0.005% by volume which is not more than 0.010% by volume (Comparative Example 4), the ETY loss ratio is increased.

Example 10, and Comparative Examples 5 and 6

A continuous low polymerization reaction of ethylene is carried out in a process having the completely mixing and stirring type reactor 10, the degassing tank 20, the ethylene separation column 30, the high boiling column 40, the hexene separation column 50 and the solvent drum 60 which stores a circulation solvent, wherein the recovered n-heptane separated in the hexene separation column 50 is passed through the solvent drum 60 sealed with nitrogen to 2 kgf/cm$^2$, and then continuously supplied to the reactor at a flow rate of 34 liters/hr, as shown in FIG. 1.

The amount of gas discharged from the gas discharge line 10b set to the reactor 10 is changed such that a nitrogen concentration in the gas phase part of the reactor 10 is the value shown in Table 3, and the ethylene loss ratio (ETY loss ratio) and the catalyst efficiency (CE) are obtained. The results are shown in Table 3.

TABLE 3

| | | Nitrogen concentration in gas phase part of reactor (% by volume) | ETY loss ratio (%) | Catalyst efficiency (CE) |
|---|---|---|---|---|
| Example | 10 | 1.200 | 1.130 | 510000 |
| Comparative Example | 5 | 68.50 | 0.024 | 110000 |
| Comparative Example | 6 | 0.007 | 66 | 520000 |

It is seen from the results shown in Table 3 that when the concentration of nitrogen contained in the gas phase of the reactor 10 is in a range of from 0.010 to 50.00% by volume (1.200% by volume: Example 10), the ETY loss ratio is low, and the catalyst efficiency is high.

Contrary to this, when the concentration of nitrogen contained in the gas phase of the reactor 10 is 68.50% by volume which is not less than 50.00% by volume (Comparative Example 5), the catalyst efficiency is decreased. Furthermore, when the concentration of nitrogen contained in the gas phase of the reactor 10 is 0.007% by volume which is not more than 0.010% by volume (Comparative Example 6), the ETY loss ratio is increased.

In the Examples and Comparative Examples, nitrogen gas is used as the inert gas, but it can be expected that the same result is obtained even in the use of a rare gas such as argon. The reason for this is not always clear, but because the rare gas such as helium has the solubility higher than that of nitrogen, there is the possibility that if the rare gas is dissolved in a catalyst solution and a solvent even in a slight amount, the rare gas is accumulated in the reaction system. Therefore, the rare gas must be purged outside the system.

While the invention has been described in detail and with reference to the specific embodiments thereof, it will be apparent to one skilled in the art that various changes and modifications can be made therein without departing from the spirit and scope thereof.

This application is based on Japanese Patent Application (Patent Application No. 2006-354541) filed Dec. 28, 2006, the entire contents thereof being hereby incorporated by reference.

INDUSTRIAL APPLICABILITY

According to the present invention, an α-olefin low polymer can be produced in high yield. Therefore, the industrial value of the present invention is remarkable.

The invention claimed is:

1. A method of producing an α-olefin polymer, the method comprising:
    subjecting an α-olefin to polymerization reaction in a solvent supplied to a reactor in the presence of a chromium catalyst; and
    adjusting a proportion of an inert gas in a gas phase of the reactor, such that the proportion of the inert gas is from 0.010 to 50.00% by volume, to obtain an α-olefin polymer comprising 2 to 10 units of the α-olefin as a monomer in polymerized form,
    wherein:
    the inert gas is nitrogen, a rare gas, or a mixture thereof;
    an unreacted α-olefin and the solvent are separated from a reaction liquid obtained by the polymerization reaction of the α-olefin;
    the solvent separated from the reaction liquid obtained by the polymerization reaction of the α-olefin is circulated into the reactor without passing through a tank containing the inert gas, such that inert gas existing in the gas phase part of the tank is prevented from being dissolved in the solvent circulated into the reactor; and
    the unreacted α-olefin and the solvent separated from the reaction liquid are circulated into the reactor.

2. The method of claim 1, wherein the inert gas is discharged from the gas phase of the reactor, or discharged from a circulation piping of the unreacted α-olefin, or both of them.

3. The method of claim 2, wherein the chromium catalyst comprises a combination of a chromium compound (a), a nitrogen-containing compound (b) and an aluminum-containing compound (c).

4. The method of claim 2, wherein the chromium catalyst comprises a combination of a chromium compound (a), a nitrogen-containing compound (b), an aluminum-containing compound (c) and a halogen-containing compound (d).

5. The method of claim 3, wherein the low polymerization reaction of the α-olefin is conducted in a state that the chromium compound (a) and the aluminum-containing compound (c) are not previously contacted.

6. The method of claim 2, wherein the α-olefin is ethylene.

7. The method of claim 2, wherein the proportion of the inert gas is adjusted from 0.050 to 30.00% by volume.

8. The method of claim 2, wherein the proportion of the inert gas is adjusted from 0.500 to 10.00% by volume.

9. The method of claim 2, wherein the proportion of the inert gas is adjusted from 1.000 to 5.000% by volume.

10. The method of claim 1, wherein an ethylene loss ratio of the method is lower than an ethylene loss ratio of a method in which the inert gas existing in the gas phase the tank is supplied to the reactor.

11. The method of claim 10, wherein the ethylene loss ratio of the method is at least 6.6 times lower than the ethylene loss ratio of the method in which the inert gas existing in the gas phase of the tank is supplied to the reactor.

12. The method of claim 1, wherein the tank is a solvent drum.

* * * * *